United States Patent
Sako et al.

(10) Patent No.: US 9,937,114 B2
(45) Date of Patent: Apr. 10, 2018

(54) COSMETIC

(71) Applicant: SAKAI CHEMICAL INDUSTRY CO., LTD., Sakai-shi, Osaka (JP)

(72) Inventors: Emi Sako, Sakai (JP); Keita Kobayashi, Sakai (JP)

(73) Assignee: SAKAI CHEMICAL INDUSTRY CO., LTD., Osaka (JP)

( * ) Notice: Subject to any disclaimer, the term of this patent is extended or adjusted under 35 U.S.C. 154(b) by 0 days.

(21) Appl. No.: 15/327,892

(22) PCT Filed: Jul. 3, 2015

(86) PCT No.: PCT/JP2015/069288
§ 371 (c)(1),
(2) Date: Jan. 20, 2017

(87) PCT Pub. No.: WO2016/017372
PCT Pub. Date: Feb. 4, 2016

(65) Prior Publication Data
US 2017/0202759 A1  Jul. 20, 2017

(30) Foreign Application Priority Data
Jul. 29, 2014 (JP) .................. 2014-153700

(51) Int. Cl.
*A61K 8/02* (2006.01)
*A61K 8/29* (2006.01)
*A61Q 1/12* (2006.01)

(52) U.S. Cl.
CPC . *A61K 8/29* (2013.01); *A61Q 1/12* (2013.01)

(58) Field of Classification Search
CPC .................... A61K 8/29; A61Q 1/12
See application file for complete search history.

(56) References Cited

U.S. PATENT DOCUMENTS

| | | |
|---|---|---|
| 2002/0012681 A1 | 1/2002 | George et al. |
| 2006/0168905 A1 | 8/2006 | Blanc et al. |
| 2006/0275231 A1 | 12/2006 | Dumousseux |

FOREIGN PATENT DOCUMENTS

| | | |
|---|---|---|
| JP | H3-284613 | 12/1991 |
| JP | H5-117127 | 5/1993 |
| JP | H10-330209 | 12/1998 |
| JP | H11-171540 | 6/1999 |
| JP | 2003-500429 | 1/2003 |
| JP | 2006-505659 | 2/2006 |
| JP | 2006-316065 | 11/2006 |
| JP | 2010-265448 A | 11/2010 |

OTHER PUBLICATIONS

International Search Report, dated Sep. 15, 2015, International Patent Application No. PCT/JP2015/069288 with English translation (5 pages).
Hahn et al., "New aspects of the luminescence of magnesiumtitanate part II: activation with manganese" Journal of Luminescence, 8, pp. 318-325, 1974.

*Primary Examiner* — Nannette Holloman
(74) *Attorney, Agent, or Firm* — Hamre, Schumann, Mueller & Larson, P.C.

(57) ABSTRACT

An object of the present disclosure is to investigate fluorescent substance being safe and having a high color developing property, and obtain an inorganic red fluorescent substance consisting of an element which exerts no bad influence upon human bodies.

A cosmetic containing inorganic particles consisting of a compound represented by a general formula:

$$Mg_xTi_yO_{(x+2y+2z)}:Mn^{4+}_z$$

wherein $1.5<x<2.5$, $0.5<y\leq1.5$, and $0.0001<z<0.1$.

11 Claims, 3 Drawing Sheets

COSMETIC

TECHNICAL FIELD

The present disclosure relates to a cosmetic containing a magnesium titanate composite oxide.

BACKGROUND OF THE DISCLOSURE

It is known that a fluorescent substance is mixed in a cosmetic (for example, patent document 1). Such cosmetic is expected that the color of skin is adjusted by color development derived from the fluorescent substance and an unconventional cosmetic property is expressed by specific color derived from the fluorescence. Especially, a compound having a red fluorescence is expected to produce an effect of making the facial color appear bright by providing reddish tint to the skin.

However, an organic fluorescent substance such as 3-hydroxypyrene-5,8,10-trisulfonic acid which has been proposed, and an inorganic fluorescent substance such as NaCl:Mn have not been used substantially because they are composed of elements and molecules causing the risk of adverse influence for the human body and their safety is not confirmed. On the other hand, mineral-based fluorescent substances such as axinite (aluminum calcium borosilicate), calcite (calcium carbonate), and petalite (aluminum lithium silicate) that are considered relatively safe have been proposed (see patent document 2) but they may not be used in a cosmetic because of an insufficient color development.

A compound represented by $Mg_2TiO_4:Mn^{4+}$ has been known (for example, patent document 3 and nonpatent document 1. However, the compound of patent document 3 has been investigated as a fluorescent substance for LED and has not been known as a cosmetic component.

Patent document 4 discloses that a composite metal compound is used as an ultraviolet absorbing agent. However, patent document 4 discloses only general description about very wide compounds, and never discloses specific description about compounds having fluorescence.

PRIOR TECHNICAL DOCUMENTS

Patent Documents

[Patent Document 1] Japanese Kokai Publication Hei5-117127
[Patent Document 2] Japanese Kohyo Publication 2003-500429
[Patent Document 3] Japanese Kokai Publication 2010-265448
[Patent Document 4] Japanese Kokai Publication Hei11-171540

Nonpatent Document

[Nonpatent Document 1] J. STADE et al, "New aspects of the luminescence of magnesium titanate part II: activation with manganese" Journal of Luminescence, 8, p 318-325 (1974)

SUMMARY OF INVENTION

Problems to be Solved by the Invention

The inventors have investigated a fluorescent substance being safe and having a high color developing property, and further have investigated to obtain an inorganic red fluorescent substance consisting of an element which exerts no bad influence upon human bodies.

Means for Solving Object

The present disclosure relates to a cosmetic containing inorganic particles consisting of a compound represented by a general formula:

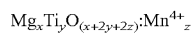
$$Mg_xTi_yO_{(x+2y+2z)}:Mn^{4+}{}_z$$

wherein $1.5<x<2.5$, $0.5<y\leq1.5$, and $0.0001<z<0.1$.

The inorganic particle content is preferably 0.1 to 90 wt % relative to the total amount of the cosmetic.

The inorganic particles preferably have a spherical shape.

The inorganic particles preferably have an average particle diameter of 1 to 200 μm.

The inorganic particles preferably have a luminance Y of 0.1 or more when a light having an excitation light wavelength of 365 nm is irradiated.

Effects of the Invention

The cosmetic of the present disclosure has an excellent color developing property and a high safety.

DETAILED DESCRIPTION OF PREFERRED EMBODIMENTS

Figure 1:
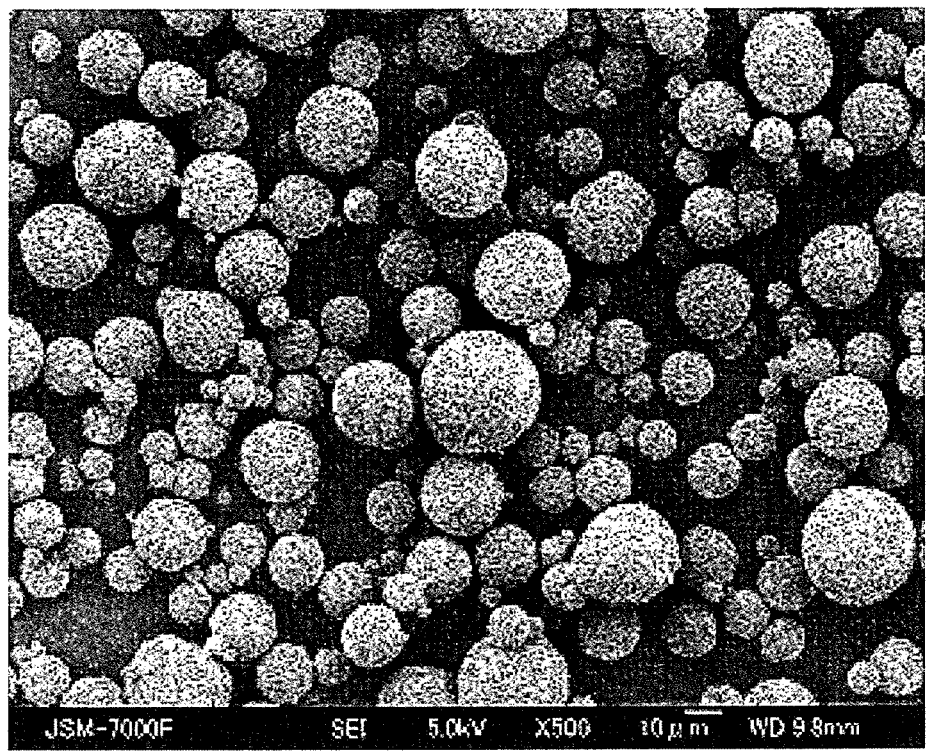
FIG. 1 is a SEM photograph of particles obtained in Example 1 (magnification: 500 magnifications).

The present disclosure relates to a cosmetic containing inorganic particles (hereinafter referred to as inorganic particles of the present disclosure) consisting of a compound represented by a general formula: $Mg_xTi_yO_{(x+2y+2z)}:Mn^{4+}{}_z$ (in the formula, $1.5<x<2.5$, $0.5<y\leq1.5$, and $0.0001<z<0.1$). That is, the cosmetic contains inorganic particles consisting of a compound obtained by doping a compound represented by a general formula $Mg_xTi_yO_{(x+2y)}$ with $Mn^{4+}$. $Mg_2TiO_4:Mn^{4+}$ fluorescent substance had been developed in 1948 (nonpatent document 1).

Recently, research and development of $Mg_2TiO_4:Mn^{4+}$ as red fluorescent substance for white LED have been carried out. However, such red fluorescent compound has not been examined as a material for a cosmetic.

The inventors completed the present disclosure by founding that the inorganic particle of the present disclosure may be used suitably as a material for a cosmetic. That is, the inorganic particle of the present disclosure is safe material which is harmless to human health, and has a high stability and an excellent red color developing property when used. Therefore, a cosmetic showing an unprecedented and good cosmetic appearance can be obtained.

The inorganic particle of the present disclosure satisfies the requirement that x, y, and z in the formula are within the above-mentioned range. The x, y, and z are preferably set within the following range because a suitable fluorescent properties may be achieved.

The lower limit of x is more preferably 1.8 and the upper limit of x is more preferably 2.2.

The lower limit of y is more preferably 0.8 and the upper limit of y is more preferably 1.2.

The lower limit of z is more preferably 0.001 and the upper limit of z is more preferably 0.05.

The lower limit of x/(y+z) is preferably 1.5, and more preferably 1.9. The upper limit thereof is preferably 2.7, and more preferably 2.1.

The inorganic particles of the present disclosure preferably have a luminance Y in xyz representation system of 0.1 or more when a light having an excitation light wavelength of 365 nm is irradiated. When the inorganic particle having a luminance Y of less than 0.1 are used in a cosmetic, the reddish tint is hardly recognized. The luminance Y depends on the composition and additives mentioned later, so that the luminance Y may be set at 0.1 or more by adjusting the above-mentioned elements. The luminance Y is more preferably 0.3 or more, and still more preferably 0.5 or more. In this specification, the luminance Y is measured by the method disclosed in the example.

The inorganic particle of the present disclosure may contains alkaline metals such as Li, Na, and K, alkaline earth metals such as Be, Ca, Sr, Ba, and Ra, other metals such as Y, Zr, V, Nb, Cr, Mo, W, Fe, Co, Ni, Pd, Pt, Cu, Ag, Zn, B, Al, Ga, Si, Ge, Sn, Pb, P, and Gd, and nonmetals such as S within such a range as not to affect safety for a human body and performances. The defined content is not particularly limited but the content of the other metal is preferably 10 wt % or less relative to the inorganic particle of the present disclosure.

The shape and particle diameter of the inorganic particle of the present disclosure are not particularly limited and an inorganic particle having a spherical shape may be used. The spherical particles is preferred because the particles have excellent performances in the feeling when applied to the skin so that the particles can be especially suitable for a material of a cosmetic.

More specifically, the spherical particles preferably have an aspect ratio of 1.00 to 1.50, more preferably 1.00 to 1.30. As long as the aspect ratio of the whole particles measured by the measurement method described in detail later is within the above-mentioned range, nonspherical particles (for example, particle obtained by necking plural particles, and elliptical particles obtained by taking the next particles) having an aspect ratio of over 1.50 may be contained in a range not to exert any influence upon the particle performances. The amount of the nonspherical particle is preferably 10% or less (in terms of number) relative to the whole inorganic particles of the present disclosure, more preferably 5% or less, and still more preferably 1% or less. In addition, the aspect ratio is a value obtained by measuring the long diameter of 2000 particles and the short diameter orthogonal to the long diameter at the middle point of the long diameter in a SEM photograph with 500 magnification and dividing the long diameter by the short diameter.

An average particle diameter (D50) of the inorganic particles of the present disclosure is preferably 1 to 200 μm, more preferably 1 to 50 μm. Further, D90/D50 of the particles is preferably 3 or less. When D50 is less than 1 μm, the emission intensity is reduced. When D50 is more than 200 μm and D90/D50 is more than 3, there are too many coarse particles so that the feeling of roughness may be occurred if the particles are used in a cosmetic. A method for measuring the particle diameter includes centrifugal settling method, electrozone method, diffraction/scattering method, image analysis method of SEM photograph, and so on.

The inorganic particles of the present disclosure preferably have a BET specific surface area of 0.03 to 1.5 $m^2/g$. When the BET specific surface area is less than 0.03 $m^2/g$, the emission intensity may be reduced. When the BET specific surface area is more than 1.5 $m^2/g$, the emission intensity may be reduced.

The inorganic particles of the present disclosure may be primary particles or coagulated particles obtained by coagulating the primary particles. The coagulated particles are preferred because the particles diameter thereof can be easily increased or the shape thereof can be easily changed to spherical shape. In addition, when the inorganic particle of the present disclosure are coagulated particles, the aspect ratio is measured on the basis of coagulated particles.

A method for producing the inorganic particles of the present disclosure is not particularly limited but the particles may be obtained by a method comprising a step of mixing a Mg source compound, a Mn source compound, and a Ti source compound as the raw material in accordance with the mole ratio of the intended compound to prepare a precursor and a step of calcinating.

The Mg source compound may include magnesium carbonate, magnesium hydroxide, magnesium oxide, magnesium chloride, magnesium nitrate, magnesium sulfate, magnesium fluoride, magnesium bromide, and magnesium iodide. Two or more of these compounds may be used in combination.

The Ti source compound may include titanium oxide, titanium tetrachloride, titanium sulfate, and titanium hydroxide. Two or more of these compounds may be used in combination.

The Mn source compound may include manganese carbonate, manganese acetate, manganese oxide, manganese sulfate, manganese nitrate, manganese fluoride, and manganese bromide. Two or more of these compounds may be used in combination.

A flux component may be used according to need at the time of calcinating.

A method for mixing these material compounds may be any known method. For example, a method which comprises preparing a water-based dispersion of the material compound and stirring or mixing by using a wet media mill such as an aqua mill and a planetary ball mill and then evaporative drying the whole quantity, or a method which comprises dry mixing using a general mixing apparatus such as a henschel mixer, and a tumbler, or a hammer mill, a high pressure air jet mill, or a combination thereof may be used.

It is preferred to obtain the inorganic particles of the present disclosure which have a spherical shape and a particle diameter (D50) of 1 μm or more by a method drying the above-mentioned water-based dispersion by using a spray drier to obtain a precursor and calcinating the precursor.

A calcinating method of the precursor obtained by the above-mentioned method may be any known method. For example, a method of calcinating with a ceramics crucible or a method of calcinating with a rotary kiln while rotating may be used.

The calcinating is preferably performed under oxidizing calcinating condition such as in the atmosphere. A calcinating temperature is not particularly limited but preferably 1100 to 1800° C., more preferably 1150 to 1600° C. When the temperature is not more than 1100° C., the emission intensity may become very weak because it becomes easy to generate $MgTiO_3$. Therefore, it is preferred that the calcinating is proceeded at 1150° C. or more to cause a phase change to $Mg_2TiO_4$. When the temperature is more than 1800° C., the particles may be strongly sintered to deteriorate the dispersibility, and the emission intensity may be reduced because of the lowering of the surface area.

The particles after calcinating may be subjected to post-treatments such as filtration through a sieve, water, acid, or alkali washing, and pulverization as necessary. The particles obtained by repeating once or more times the steps of calcinating after calcinating are especially preferred because they have an improved emission intensity.

It is especially preferred that the first calcinating is performed at the above mentioned range of the temperature, and the second calcinating is performed at 400 to 1000° C.

The inorganic particle of the present disclosure may be blended in a cosmetic as it is but may be subjected to any known surface treatment according to need before blending.

The surface treatment is not particularly limited but any material may be used for the surface treatment if the material can be used for a cosmetic. A coating layer composed of inorganic compounds such as oxides, hydroxides, carbonates, and phosphates of silicone, zinc, titanium, aluminum, zirconium, and tin may be provided. Further, for giving water repellency, dimethylpolysiloxane, methylhydrogenpolysiloxane, methylphenylpolysiloxane, methylmethoxypolysiloxane, dimethylpolysiloxane dihydrogen, and copolymers thereof, stearic acid, lauric acid, oleic acid, and metal salts thereof (aluminum salt, zinc salt, magnesium salt, and calcium salt), polyvinyl alcohol, ethylene glycol, propylene glycol, monoethanolamine, aminomethylpropanol, diethanolamine, triethanolamine, monopropanolamine, dipropanolamine, tripropanolamine, paraffin wax, polyethylene wax, aminosilane, epoxysilane, methacrylsilane, vinylsilane, mercaptosilane, chloroalkylsilane, alkylsilane, fluoroalkylsilane, hexamethylsilazane, hexamethylcyclotrisilazane, trimethylolpropane, trimethylolethane, and pentaerythritol may be included.

The surface treatment may be performed using a single compound, a lamination process or a mixing process may be performed by using two or more compounds in combination. Further, a coating layer of an organic compound may be provided after the treatment of the inorganic compound, but it is important not to reduce the original emission property.

The coating amount of the inorganic compound and the organic compound is preferably 0.1 to 30 wt % relative to the inorganic particles, more preferably 0.1 to 20 wt %. When the coating amount is 0.1 wt % or more, the function improving effect by the surface treatment can be exerted. When the coating amount is 30 wt % or less, the treatment may be performed without damaging the original emission property, and it is advantageous from economic viewpoint.

A method of the surface treatment is not particularly limited but may be performed by a method comprising adding the inorganic compound or the organic compound to a water-based dispersion of the inorganic particles and then adjusting the pH of the dispersion to coat. Further, water-insoluble organic compounds may be surface-treated by dry mixing an organic compound, and pulverizing or mixing followed by heating according to need for coating the water-insoluble organic compound.

The cosmetic of the present disclosure preferably contains the inorganic particles of the present disclosure of 0.1 to 90 wt %. When the content is less than 0.1 wt %, the above-mentioned effect may not be obtained sufficiently. When the content is over 90 wt %, it is not preferred because the content of the powder becomes excess so that the degree of freedom for cosmetic composition is reduced to make the composition design difficult, for example the content of liquid components becomes insufficient. The content is more preferably 0.1 to 50 wt %, still more preferably 0.1 to 30 wt %.

Examples of the cosmetic of the present disclosure may include a foundation, a makeup base, an eye shadow, a rouge, a mascara, a lipstick and a sunscreen agent. The cosmetic of the present disclosure can be in any form such as that of an oil-based cosmetic, a water-based cosmetic, an O/W type cosmetic or a W/O type cosmetic. Above all, the cosmetic of the present disclosure can be suitably used in makeup cosmetics including a foundation, a makeup base, and an eye shadow and sunscreen agents.

For the cosmetic of the present disclosure, any aqueous component or oily component that can be used in the field of cosmetics can be used in combination in addition to the inorganic particle of the present disclosure. The aqueous component and oily component described above are not particularly limited, and examples thereof may include those containing components such as oils, surfactants, moisturizers, higher alcohols, sequestrants, natural and synthetic polymers, water-soluble and oil-soluble polymers, UV blocking agents, various extracts, inorganic and organic pigments, inorganic and organic clay minerals and other various powders, inorganic and organic pigments treated with metallic soap or silicone, coloring materials such as organic dyes, preservatives, antioxidants, dyes, thickeners, pH adjusters, perfumes, cooling-sensation agents, antiperspirants, disinfectants, and skin activators. Specifically, a desired cosmetic can be produced in the usual manner using any one or more of the components listed below. The amounts of these components incorporated are not particularly limited as long as they do not interfere with the effects of the present invention.

The oil is not particularly limited, and examples thereof may include avocado oil, *camellia* oil, turtle oil, macadamia nut oil, corn oil, mink oil, olive oil, rapeseed oil, egg-yolk oil, sesame oil, persic oil, wheat germ oil, sasanqua oil, castor oil, linseed oil, safflower oil, cottonseed oil, *perilla* oil, soybean oil, *arachis* oil, tea seed oil, kaya oil, rice bran oil, Chinese tung oil, Japanese tung oil, jojoba oil, germ oil, triglycerol, glycerol trioctanoate, glycerol triisopalmitate, cacao butter, coconut oil, horse fat, hydrogenated coconut oil, palm oil, beef tallow, mutton tallow, hydrogenated beef tallow, palm kernel oil, lard, beef bone fat, Japan wax kernel oil, hydrogenated oil, neatsfoot oil, Japan wax, hydrogenated castor oil, beeswax, candelilla wax, cotton wax, carnauba wax, bayberry wax, insect wax, spermaceti wax, montan wax, bran wax, lanolin, kapok wax, lanolin acetate, liquid lanolin, sugarcane wax, isopropyl lanolate, hexyl laurate, reduced lanolin, jojoba wax, hard lanolin, shellac wax, POE lanolin alcohol ether, POE lanolin alcohol acetate, POE cholesterol ether, polyethylene glycol lanolate, POE hydrogenated lanolin alcohol ether, liquid paraffin, ozokerite, pristane, paraffin, ceresin, squalene, Vaseline, and microcrystalline wax.

The lipophilic nonionic surfactant is not particularly limited, and examples thereof may include sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate; glycerin polyglycerin fatty acids such as glycerol mono-cottonseed oil fatty acid, glycerol monoerucate, glycerol sesquioleate, glycerol monostearate, α,α'-glycerol oleate pyroglutamate, and glycerol monostearate malate; propylene glycol fatty acid esters such as propylene glycol monostearate; hydrogenated castor oil derivatives; and glycerol alkyl ethers.

The hydrophilic nonionic surfactant is not particularly limited, and examples thereof may include POE sorbitan fatty acid esters such as POE sorbitan monooleate, POE sorbitan monostearate and POE sorbitan tetraoleate; POE sorbitol fatty acid esters such as POE sorbitol monolaurate, POE sorbitol monooleate, POE sorbitol pentaoleate and POE sorbitol monostearate; POE glycerin fatty acid esters such as POE glycerin monostearate, POE glycerin monoisostearate and POE glycerin triisostearate; POE fatty acid esters such as POE monooleate, POE distearate, POE monodioleate and ethylene glycol distearate; POE alkyl ethers such as POE lauryl ether, POE oleyl ether, POE stearyl ether, POE behenyl ether, POE 2-octyldodecyl ether and POE cholestanol ether; POE alkyl phenyl ethers such as POE octyl phenyl ether, POE nonyl phenyl ether and POE dinonyl phenyl ether; Pluaronic types such as Pluronic; POE/POP alkyl ethers such as POE/POP cetyl ether, POE/POP 2-decyltetradecyl ether, POE/POP monobutyl ether, POE/POP hydrogenated lanolin and POE/POP glycerin ether; tetra-POE/tetra-POP ethylenediamine condensation products such as Tetronic; POE castor oil hydrogenated castor oil derivatives such as POE castor oil, POE hydrogenated castor oil, POE hydrogenated castor oil monoisostearate, POE hydrogenated castor oil triisostearate, POE hydrogenated castor oil monopyroglutamic acid monoisostearic acid diester and POE hydrogenated castor oil maleic acid; POE beeswax/lanolin derivatives such as POE sorbitol beeswax; alkanolamides such as coconut oil fatty acid diethanolamide, lauric acid monoethanolamide and fatty acid isopropanol amide; POE propylene glycol fatty acid esters; POE alkylamines; POE fatty acid amides; sucrose fatty acid esters; POE nonylphenyl formaldehyde condensation products; alkyl ethoxy dimethylamine oxides; and trioleyl phosphoric acid.

Examples of other surfactants include anionic surfactants such as fatty acid soaps, higher-alkyl sulfuric ester salts, POE triethanolamine lauryl sulfate, and alkyl ether sulfuric ester salts; cationic surfactants such as alkyl trimethylammonium salts, alkyl pyridinium salts, alkyl quaternary ammonium salts, alkyl dimethylbenzyl ammonium salts, POE alkylamines, alkylamine salts, and polyamine fatty acid derivatives; and amphoteric surfactants such as imidazoline amphoteric surfactants and betaine surfactants. They may be incorporated within the bounds of not causing any problems with stability and skin irritation.

The moisturizer is not particularly limited, and examples thereof may include xylitol, sorbitol, maltitol, chondroitin sulfate, hyaluronic acid, mucoitinsulfuric acid, caronic acid, atelocollagen, cholesteryl-12-hydroxystearate, sodium lactate, bile salts, dl-pyrrolidone carboxylate, short-chain soluble collagens, diglycerol (EO) PO adducts, *Rosa roxburghii* extract, yarrow extract, and melilot extract.

The higher alcohol is not particularly limited, and examples thereof may include linear alcohols such as lauryl alcohol, cetyl alcohol, stearyl alcohol, behenyl alcohol, myristyl alcohol, oleyl alcohol, and cetostearyl alcohol; and branched alcohols such as monostearyl glycerol ether (batyl alcohol), 2-decyltetradecynol, lanolin alcohol, cholesterol, phytosterol, hexyldodecanol, isostearyl alcohol, and octyldodecanol.

The sequestrant is not particularly limited, and examples thereof may include 1-hydroxyethane-1,1-diphosphonic acid, 1-hydroxyethane-1,1-diphosphonic acid tetrasodium salt, sodium citrate, sodium polyphosphate, sodium metaphosphate, gluconic acid, phosphoric acid, citric acid, ascorbic acid, succinic acid, and edetic acid.

The natural water-soluble polymer is not particularly limited, and examples thereof may include plant-derived polymers such as gum arabic, tragacanth gum, galactan, guar gum, carob gum, karaya gum, carrageenan, pectin, agar, quince seed (quince), algal colloid (algal extract), starch (rice, corn, potato, wheat), and glycyrrhizinic acid; microorganism-derived polymers such as xanthan gum, dextran, succinoglucan, and pullulan; and animal-derived polymers such as collagen, casein, albumin, and gelatin.

The semisynthetic water-soluble polymer is not particularly limited, and examples thereof may include starch polymers such as carboxymethyl starch and methyl hydroxypropyl starch; cellulose polymers such as methyl cellulose, nitro cellulose, ethyl cellulose, methyl hydroxypropyl cellulose, hydroxyethyl cellulose, cellulose sodium sulfate, hydroxypropyl cellulose, sodium carboxymethylcellulose (CMC), crystalline cellulose, and cellulose powder; and alginate polymers such as sodium alginate and propylene glycol alginate.

The synthetic water-soluble polymer is not particularly limited, and examples thereof may include vinyl polymers such as polyvinyl alcohol, polyvinyl methyl ether, and polyvinyl pyrrolidone; polyoxyethylene polymers such as polyethylene glycol 20,000, polyethylene glycol 40,000, and polyethylene glycol 60,000; copolymers such as polyoxyethylene-polyoxypropylene copolymers; acrylic polymers such as sodium polyacrylate, polyethylacrylate, and polyacrylamide; polyethyleneimine; and cationic polymers.

The inorganic water-soluble polymer is not particularly limited, and examples thereof may include bentonite, magnesium aluminum silicate (Veegum), laponite, hectorite, and silicic anhydride.

The ultraviolet blocking agent is not particularly limited, and examples thereof may include benzoic acid-based ultraviolet blocking agents such as paraaminobenzoic acid (hereinafter, abbreviated as PABA), PABA monoglycerin ester, N,N-dipropoxy PABA ethyl ester, N,N-diethoxy PABA ethyl ester, N,N-dimethyl PABA ethyl ester and N,N-dimethyl PABA butyl ester; anthranilic acid-based ultraviolet blocking agents such as homomenthyl-N-acetyl anthranilate; salicylic acid-based ultraviolet blocking agents such as amyl salicylate, menthyl salicylate, homomenthyl salicylate, octyl salicylate, phenyl salicylate, benzyl salicylate and p-isopropanol phenyl salicylate; cinnamic acid-based ultraviolet blocking agents such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate and glycerylmono-2-ethylhexanoyl-di-paramethoxy cinnamate; benzophenone-based ultraviolet blocking agents such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone and 4-hydroxy-3-carboxybenzophenone; 3-(4'-methylbenzylidene)-d,l-camphor, 3-benzylidene-d,l-camphor, urocanic acid, urocanic acid ethyl ester, 2-phenyl-5-methylbenzoxazole, 2,2'-hydroxy-5-methylphenyl benzotrialzole, 2-(2'-hydroxy-5'-t-octylphenyl)benzotriazole, 2-(2'-hydroxy-5'-methylphenyl benzotriazole, dibenzalazine, dianisoylmethane, 4-methoxy-4'-t-butyldibenzoylmethane and 5-(3,3-dimethyl-2-norbornylidene)-3-pentane-2-one.

Other components are not particularly limited, and examples thereof may include vitamins such as vitamin A oil, retinol, retinol palmitate, inositol, pyridoxine hydrochloride, benzyl nicotinate, nicotinamide, DL-α-tocopherol nicotinate, magnesium ascorbyl phosphate, 2-O-α-D-glucopyranosyl-L-ascorbic acid, vitamin D2 (ergocalciferol), DL-α-tocopherol, DL-α-tocopherol acetate, pantothenic acid, and biotin; hormones such as estradiol and ethynyl estradiol; amino acids such as arginine, aspartic acid, cystine, cysteine, methionine, serine, leucine, and tryptophan; anti-inflammatory agents such as allantoin and azulene; whitening agents such as arbutin; astringents such as tannic acid; refrigerants such as L-menthol and camphor, sulfur, lysozyme chloride, and pyridoxine chloride.

Various kinds of extracts are not particularly limited, and examples thereof may include *Houttuynia cordata* extract, Phellodendron bark extract, melilot extract, dead nettle extract, licorice extract, peony root extract, soapwort extract, luffa extract, cinchona extract, strawberry geranium extract, *sophora* root extract, *nuphar* extract, fennel extract, primrose extract, rose extract, rehmannia root extract, lemon extract, lithospermum root extract, aloe extract, calamus root extract, *eucalyptus* extract, field horsetail extract, sage extract, thyme extract, tea extract, seaweed extract, cucumber extract, clove extract, bramble extract, lemon balm extract, carrot extract, horse chestnut extract, peach extract, peach leaf extract, mulberry extract, knapweed extract, *hamamelis* extract, placenta extract, thymic extract, silk extract, and licorice extract.

Examples of the various kinds of powders may include bright coloring pigments such as red oxide, yellow iron oxide, black iron oxide, mica titanium, iron oxide-coated mica titanium and titanium oxide-coated glass flakes, inorganic powders such as those of mica, talc, kaolin, sericite, titanium dioxide and silica, and organic powders such as polyethylene powder, nylon powder, crosslinked polystyrene, cellulose powder and silicone powder. Preferably, part or all of the powder component is subjected to a known hydrophobization treatment with a substance such as a silicone, a fluorine compound, a metallic soap, an oily agent or an acyl glutamic acid salt for improvement of sensory characteristics and improvement of makeup retainability.

EXAMPLES

Hereinafter, the present disclosure will be explained with reference to examples. However, the present disclosure is not limited to these examples.
(Production Method of Inorganic Particle Consisting of a Compound Represented by $Mg_2TiO_4:Mn^{4+}$)

Example 1

Basic magnesium carbonate (GP-30N manufactured by Konoshima Chemical Co., Ltd., the content of Mg is 26.12 wt %) 1395.5 g, manganese carbonate (manufactured by Chuo Denki Kogyo Co., Ltd., purity 94.58%) 3.6461 g, and titanium oxide (A-120 manufactured by Sakai Chemical Industry Co., Ltd., purity 99.00%) 602.7 g were weighed. Then, purified water 7.5 L and zirconia beads 8 L were added and the mixture was stirred sufficiently at 250 rpm for 30 minutes by using an aqua mill. The mixed slurry was evaporative dried by using a spray drier (model name: BDP-22E manufactured by Ohkawara Kakohki Co., Ltd., disc rotation speed: 16000 rotation, outlet temperature: 105 to 110° C.) to obtain calcinating precursor powder. Next, the calcinating precursor was put in an alumina crucible and heated to 1250° C. at 200° C./hour in the atmosphere. After keeping the temperature for 10 hours, the matter was cooled to room temperature at 200° C./hour. Then, the matter was heated to 600° C. at 200° C./hour in the atmosphere and, after keeping the temperature for 24 hours, cooled to room temperature at 200° C./hour.

The electron microscope photograph of P1 thus obtained is shown in FIG. 1. When P1 is expressed by a general formula, $Mg_xTi_yO_{(x+2y+2z)}:Mn^{4+}_z$, X=2.00, y=0.996, and Z=0.004.

Example 2

Basic magnesium carbonate (GP-30N manufactured by Konoshima Chemical Co., Ltd., the content of Mg is 26.12 wt %) 9.303 g, manganese carbonate (manufactured by Chuo Denki Kogyo Co., Ltd., purity 94.58%, 0.0243 g), titanium oxide (SUPER-TITANIA manufactured by Showa Denko K.K., purity 99.92%) 3.9822 g, and purified water 50 g were weighed. Then, the mixture was stirred sufficiently at 250 rpm for 30 minutes by using a planetary ball mill. The mixed slurry was evaporative dried for one night by using a drier at 130° C. to obtain calcinating precursor powder. Next, the calcinating precursor was put in an alumina crucible and heated to 1250° C. at 200° C./hour in the atmosphere. After keeping the temperature for 10 hours, the matter was cooled to room temperature at 200° C./hour. Then, the matter was heated to 600° C. at 200° C./hour in the atmosphere and, after keeping the temperature for 24 hours, cooled to room temperature at 200° C./hour.

Figure 2:
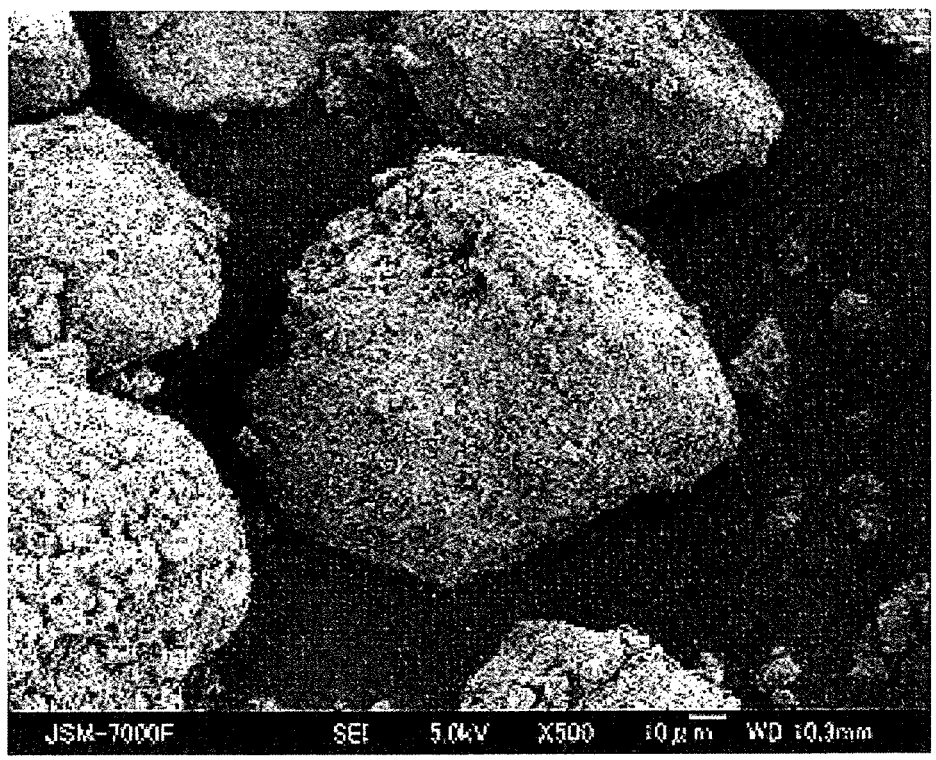
FIG. 2 is a SEM photograph of particles obtained in Example 2 (magnification: 500 magnifications).

The electron microscope photograph of P2 thus obtained is shown in FIG. 2. When P2 is expressed by a general formula, $Mg_xTi_yO_{(x+2y+2z)}:Mn^{4+}_z$, X=2.00, y=0.996, and Z=0.004.

Example 3

Basic magnesium carbonate (GP-30N manufactured by Konoshima Chemical Co., Ltd., the content of Mg is 26.12 wt %) 1395.5 g, manganese carbonate (manufactured by Chuo Denki Kogyo Co., Ltd., purity 94.58%) 3.6461 g, and titanium oxide (A-120 manufactured by Sakai Chemical Industry Co., Ltd., purity 99.00%) 602.7 g were weighed. Then, purified water 7.5 L and zirconia beads 8 L were added and the mixture was stirred sufficiently at 250 rpm for 30 minutes by using an aqua mill. The mixed slurry was evaporative dried by using a spray drier (model name: BDP-22E manufactured by Ohkawara Kakohki Co., Ltd., disc rotation speed: 16000 rotation, outlet temperature: 105 to 110° C.) to obtain calcinating precursor powder. Next, the calcinating precursor was put in an alumina crucible and heated to 1250° C. at 200° C./hour in the atmosphere. After keeping the temperature for 10 hours, the matter was cooled to room temperature at 200° C./hour. Next, the matter was put in water and pulverized sufficiently at 250 rpm for 40 minutes by using a planetary ball mill. After separating beads, coarse particles were removed bypassing through a sieve having sieve mesh of 15 μm. After filtration, the obtained matter was dried at 130° C. Then, the obtained matter was heated to 600° C. at 200° C./hour in the atmosphere and, after keeping the temperature for 24 hours, cooled to room temperature at 200° C./hour.

The electron microscope photograph of P3 thus obtained is shown in FIG. X. When P1 is expressed by a general formula, $Mg_xTi_yO_{(x+2y+2z)}:Mn^{4+}_z$ X=2.00, y=0.996, and Z=0.004.

Evaluation Example 1 (Evaluation as Fluorescent Substance)

The fluorescent samples obtained in examples were evaluated.

[Measurement of Luminance Y, Chromaticity (x, y), Excitation Spectrum, and Emission Spectrum]

The excitation spectrum and emission spectrum were measured by using FP-6500 manufactured by JASCO Corporation where the excitation wavelength was set at 365 nm and the emission wavelength was set at 657 nm. ISF-513 type was used as a fluorescent integral sphere, and the value of voltage of photomultiplier tube (PMT) was set at 340.

[Shape of Fluorescent Substance Particle]

Figure 3:
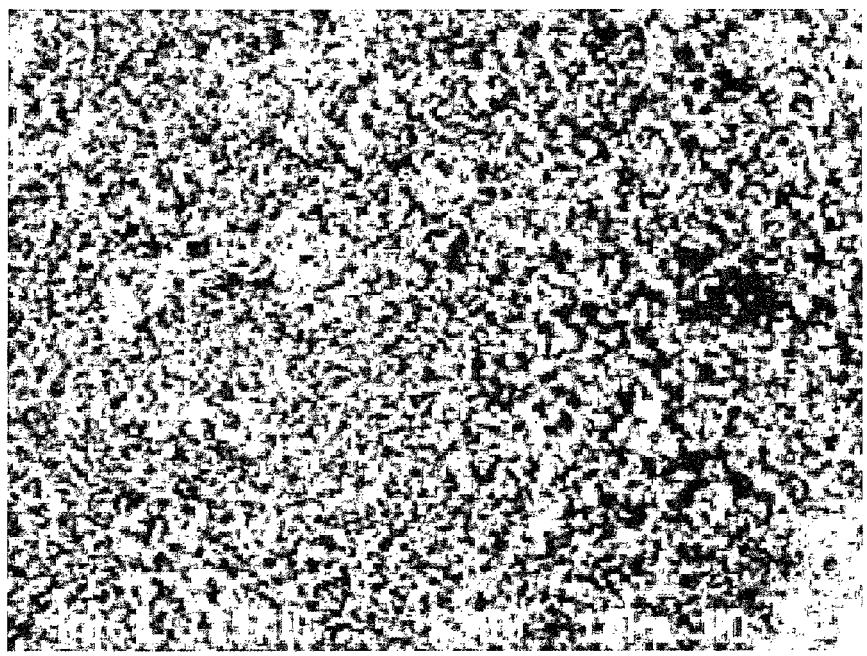
FIG. 3 is a SEM photograph of particles obtained in Example 3 (magnification: 500 magnifications).
Figure 4:
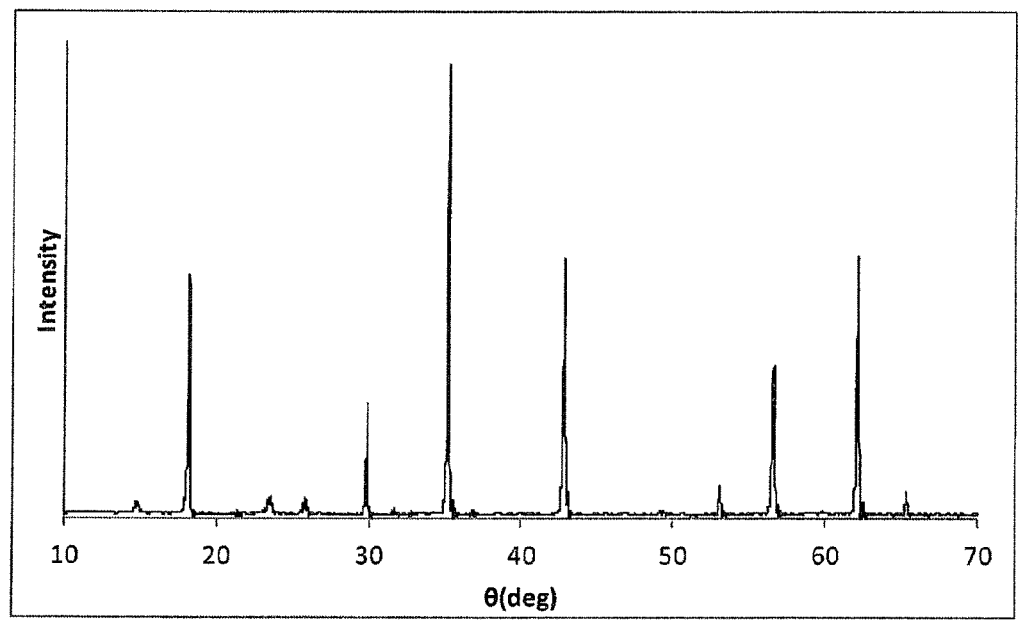
FIG. 4 is a XRD pattern of particles obtained in Example 1.
Figure 5:
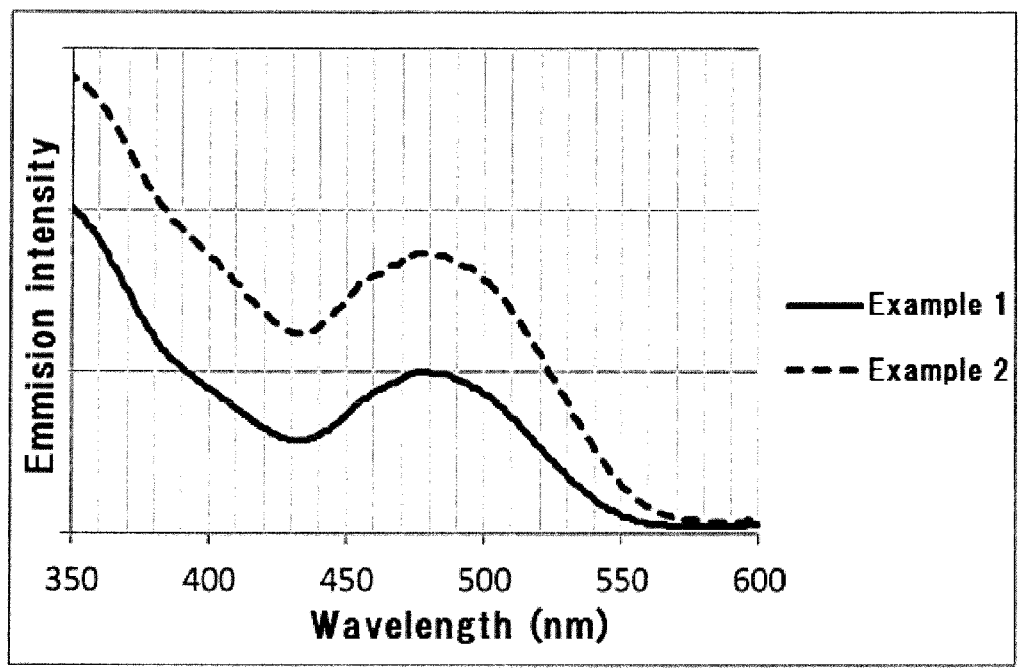
FIG. 5 is excitation spectrums of particles obtained in Examples 1 and 2.
Figure 6:
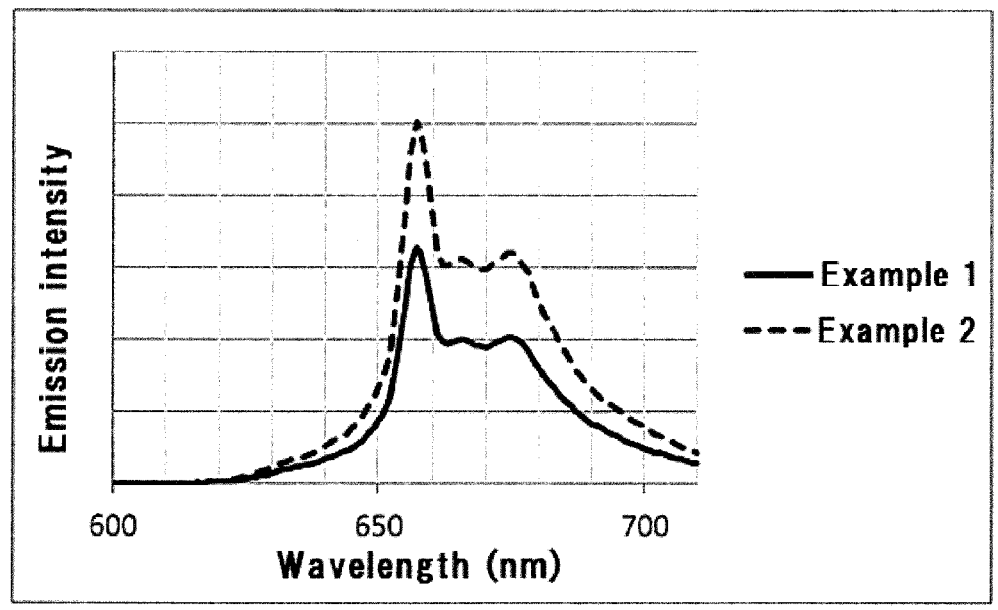
FIG. 6 is emission spectrums of particles obtained in Examples 1 and 2.

The SEM photographs of P1 to P3 were taken by using a SEM (7000F manufactured by JEOL Ltd.) for confirming the shape of the fluorescent substance particles. The results are shown in FIGS. 1 to 3. From FIG. 1, it is clear that the inorganic particles obtained in example 1 are spherical shaped.

[Identification of Fluorescent Substance]

The measurement by XRD (RINT-TTRIII manufactured by Rigaku Corporation, x-rays=CuKα, λ=1.5406 Å, 50 kV, 300 mA) was performed for identification of the product P1 obtained in example 1. The measurement result matched PDF card #01-072-6975 or #01-079-0830, and it was confirmed that the compositions of base bodies of P1, P2, and P3 were almost the same as $Mg_2TiO_4$. The result is shown in FIG. 3.

[Measurement of Specific Surface Area and Particle Size Distribution]

The specific surface area was measured by using Macsorb Model HM-1220 manufactured by Mountech Co., Ltd. at the deaeration temperature of 230° C. for the deaeration time of 35 minutes and the result was shown in table 1. The particle size distribution was measured by using a laser diffraction particle size distribution analyzer (MT-3000 manufactured by NIKKISO CO., LTD) (measurement condition: the measurement was performed by blending deionized water, a dispersant, and the sample so that the diffraction light amount (DV) is 0.01 to 0.2 with the use of sodium hexametaphosphate as the dispersant) and the result was shown in table. 1.

[Measurement of Aspect Ratio]

The long diameter of 200 particles in a SEM photograph enlarged 500 times and the short diameter defined as a diameter which is orthogonal to the long diameter at the middle point of the long diameter were measured. Next, an aspect ratio was determined by dividing the value of the long diameter by the value of the short diameter. The average value of the measured aspect ratios and the number ratio of particles having the aspect ratio of 1.5 or more were calculated.

Evaluation Example 2 (Sensory Evaluation)

The fluorescent substances P1 to P2 obtained in examples 1 to 3 were applied by ten panelists under the condition that the numbers of fluorescent substances were not noticed by the panelists. Then, the sensory test about the touch feeling was performed. The results of evaluation are shown in table 2.

TABLE 1

|  | P1 | P2 | P3 |
|---|---|---|---|
| Luminance Y | 0.8 | 1.1 | 0.5 |
| Chromaticity x | 0.7252 | 0.7255 | 0.7252 |
| Chromaticity y | 0.2748 | 0.2745 | 0.2748 |
| Specific surface area (m²/g) | 1.1 | 0.34 | 3.7 |
| Particle size D10 (μm) | 15.02 | 32.44 | 0.50 |
| Particle size D50 (μm) | 23.18 | 143.1 | 1.22 |
| Particle size D90 (μm) | 36.76 | 378.5 | 2.1 |
| D90/D50 | 1.59 | 2.65 | 1.69 |
| Average aspect ratio | 1.005 | 1.466 | — |
| Number ratio of particles having an aspect ratio of 1.5 or more (%) | 0.77 | 34.8 | — |

TABLE 2

|  | P1 | P2 | P3 |
|---|---|---|---|
| Number of persons that feel good in touch feeling | 10 | 3 | 10 |

Evaluation Example 3 (Evaluation as Cosmetic)

The compounds P1 to P2 obtained in examples 1 to 2 were used and powder foundations F1 and F2 were prepared according to the composition shown in table 3. Further, a powder foundation F3 not containing the inorganic particles of the present disclosure was prepared according to the composition shown in table 4. The materials used for the foundation were as shown in the table and the materials other than P1 and P2 were cosmetic grades.

TABLE 3

| Material | wt % | Grade |
|---|---|---|
| Mica | 24.30 | Y-2300X(manufactured by Yamaguchi Mica Co., Ltd.) |
| Sericite | 29.16 | FSE (manufactured by Sanshin Mining Ind. Co., Ltd.) |
| Plate-shaped barium sulfate | 11.70 | plate-shaped barium sulfate-H (manufactured by Sakai Chemical Industry Co., Ltd.) |
| Spherical silicone | 6.30 | KSP-105 (manufactured by Shin-Etsu Chemical Co., Ltd.) |
| Titanium oxide | 7.20 | R-3LD (manufactured by Sakai Chemical Industry Co., Ltd.) |
| Iron oxide (yellow) | 1.08 | Yellow iron oxide (manufactured by PINOA Co., Ltd.) |
| Iron oxide (red) | 0.36 | Red iron oxide (manufactured by PINOA Co., Ltd.) |
| Metal soap | 0.90 | JPM-100 (manufactured by Sakai Chemical Industry Co., Ltd.) |
| Oil | 9.00 | KF96 (manufactured by Shin-Etsu Chemical Co., Ltd.) |
| P1 or P2 | 10.00 |  |
| Total | 100 |  |

TABLE 4

| Material | wt % | Grade |
|---|---|---|
| Mica | 27.00 | Y-2300X(manufactured by Yamaguchi Mica Co., Ltd.) |
| Sericite | 32.40 | FSE (manufactured by Sanshin Mining Ind. Co., Ltd.) |
| Plate-shaped barium sulfate | 13.00 | plate-shaped barium sulfate-H (manufactured by Sakai Chemical Industry Co., Ltd.) |
| Spherical silicone | 7.00 | KSP-105 (manufactured by Shin-Etsu Chemical Co., Ltd.) |
| Titanium oxide | 8.00 | R-3LD (manufactured by Sakai Chemical Industry Co., Ltd.) |
| Iron oxide (yellow) | 1.20 | Yellow iron oxide (manufactured by PINOA Co., Ltd.) |
| Iron oxide (red) | 0.40 | Red iron oxide (manufactured by PINOA Co., Ltd.) |
| Metal soap | 1.00 | JPM-100 (manufactured by Sakai Chemical Industry Co., Ltd.) |
| Oil | 10.00 | KF96 (manufactured by Shin-Etsu Chemical Co., Ltd.) |
| Total | 100 | |

These materials were weighed according to the composition and mixed while stirring by a coffee mill for one minute and 30 seconds. The obtained powder mixture 0.8 g was weighed in a metal mold with a diameter of 20 mmΦ and pressed using a press machine under a pressure of 200 kgf/cm² for 30 seconds to obtain powder foundations F1 to F3.

The powder foundations F1 to F3 were applied by ten panelists under the condition that the numbers of foundations were not noticed by the panelists. Then, the color was tested with the irradiation of black light at 365 nm. The results of evaluation into five levels of reddish tint are shown in table 5. The evaluation criteria are summarized as follows 5: 8 or more or all panelists recognized reddish tint.
4: 5 to 7 panelists recognized reddish tint.
3: 2 to 4 panelists recognized reddish tint.
2: one panelist recognized reddish tint.
1: No panelist recognized reddish tint.

TABLE 5

| | F1 | F2 | F3 |
|---|---|---|---|
| The degree of reddish tint | 5 | 5 | 1 |

The powder foundations F1 to F3 were applied by ten panelists under the condition that the numbers of foundations were not noticed by the panelists. Then, the color was tested outdoors under natural light. The results of evaluation into five levels of reddish tint are shown in table 6.

TABLE 6

| | F1 | F2 | F3 |
|---|---|---|---|
| The degree of reddish tint | 4 | 4 | 1 |

The powder foundations F1 to F3 were applied by ten panelists under the condition that the numbers of foundations were not noticed by the panelists. Then, the color was tested indoors with the irradiation of LED lamp and so on. The results of evaluation into five levels of reddish tint are shown in table 7.

TABLE 7

| | F1 | F2 | F3 |
|---|---|---|---|
| The degree of reddish tint | 3 | 4 | 1 |

It is revealed that P1 and P2 show strong reddish tint by applying the values of chromaticity x and y to a chromaticity diagram. In addition, the luminance Y values of P1 and P2 are almost 1, being high. From the results of excitation spectrum, it is shown that P1 and P2 are excited by the irradiation not only an ultraviolet light but also a visible light. Further, when P1 and P2 are compounded in a cosmetic, a reddish tint may be increased in all cases of under natural light outdoors, under fluorescent light indoors, and under LED light so that a good cosmetic appearance may be obtained. From these results, it became clear that the inorganic particles of the present disclosure can improve optical functions. Furthermore, P1 having a spherical shape has an excellent property in touch feeling.

INDUSTRIAL APPLICABILITY

The cosmetic of the present disclosure may have excellent effects in covering color of the skin, imparting transparency and elasticity to the skin, and making the skin color look beautiful by correcting the color so that it can be used suitably as makeup cosmetics including a foundation.

The cosmetic of the present disclosure can exert the effect under natural light especially outside because the reddish tint becomes strong when an ultraviolet ray of 365 nm contained in natural light (sunlight) is irradiated. In addition, the cosmetic can exert the effect even indoors and when flashes or strobes are used in taking a picture because emission is generated in the visible region.

The invention claimed is:

1. A cosmetic containing inorganic particles consisting of a compound represented by a general formula:

$$Mg_xTi_yO_{(x+2y+2z)}:Mn^{4+}_z$$

wherein $1.5 < x < 2.5$, $0.5 < y \leq 1.5$, and $0.0001 < z < 0.1$.

2. The cosmetic according to claim 1 having the inorganic particle content of 0.1 to 90 wt% relative to the total amount of the cosmetic.

3. The cosmetic according to claim 1, wherein the inorganic particles have a spherical shape.

4. The cosmetic according to claim 1, the inorganic particles have an average particle diameter of 1 to 200 μm.

5. The cosmetic according to claim 1, the inorganic particles have a luminance Y of 0.1 or more when a light having an excitation light wavelength of 365 nm is irradiated.

6. The cosmetic according to claim 2, wherein the inorganic particles have a spherical shape.

7. The cosmetic according to claim 2, the inorganic particles have an average particle diameter of 1 to 200 μm.

8. The cosmetic according to claim 3, the inorganic particles have an average particle diameter of 1 to 200 μm.

9. The cosmetic according to claim 2, the inorganic particles have a luminance Y of 0.1 or more when a light having an excitation light wavelength of 365 nm is irradiated.

10. The cosmetic according to claim 3, the inorganic particles have a luminance Y of 0.1 or more when a light having an excitation light wavelength of 365 nm is irradiated.

11. The cosmetic according to claim 4, the inorganic particles have a luminance Y of 0.1 or more when a light having an excitation light wavelength of 365 nm is irradiated.

* * * * *